(12) United States Patent
Jamnia et al.

(10) Patent No.: US 8,678,820 B2
(45) Date of Patent: Mar. 25, 2014

(54) HANDPIECE FOR A MAGNETOSTRICTIVE POWER GENERATOR

(75) Inventors: Mohammad Ali Jamnia, Pleasant Prairie, WI (US); William L. Bollig, Elk Grove Village, IL (US); David W. Tipton, Rolling Meadows, IL (US)

(73) Assignee: Hu-Friedy Mfg. Co., LLC., Chicago, IL (US)

( * ) Notice: Subject to any disclaimer, the term of this patent is extended or adjusted under 35 U.S.C. 154(b) by 519 days.

(21) Appl. No.: 12/922,399

(22) PCT Filed: Mar. 18, 2008

(86) PCT No.: PCT/US2008/057328
§ 371 (c)(1),
(2), (4) Date: Feb. 25, 2011

(87) PCT Pub. No.: WO2009/116994
PCT Pub. Date: Sep. 24, 2009

(65) Prior Publication Data
US 2011/0177474 A1   Jul. 21, 2011

(51) Int. Cl.
*A61C 1/07* (2006.01)
(52) U.S. Cl.
USPC .......................................... 433/119
(58) Field of Classification Search
USPC ......... 433/25–166; 606/169; 604/22; 29/605; 361/157
See application file for complete search history.

(56) References Cited

U.S. PATENT DOCUMENTS

| | | | | |
|---|---|---|---|---|
| 3,085,185 A | * | 4/1963 | Jacke et al. | 318/116 |
| 3,419,776 A | * | 12/1968 | Kuris et al. | 318/118 |
| 3,488,851 A | * | 1/1970 | Haydu | 433/86 |
| 4,110,908 A | * | 9/1978 | Cranston | 433/125 |
| 4,768,496 A | * | 9/1988 | Kreizman et al. | 606/128 |
| 4,820,152 A | * | 4/1989 | Warrin et al. | 433/86 |
| 5,382,162 A | | 1/1995 | Sharp | |
| 5,451,161 A | * | 9/1995 | Sharp | 433/119 |
| 5,730,594 A | * | 3/1998 | Sharp | 433/119 |

(Continued)

FOREIGN PATENT DOCUMENTS

| | | |
|---|---|---|
| EP | 1279380 A1 | 1/2003 |
| WO | WO-2006/089104 A1 | 8/2006 |
| WO | WO 2008008782 A2 * | 1/2008 ............ A61C 17/20 |
| WO | WO-2008/021507 A2 | 2/2008 |

OTHER PUBLICATIONS

International Search Report and Written Opinion for corresponding International Application No. PCT/US2008/057328, dated Mar. 10, 2009.

*Primary Examiner* — Heidi M Eide
*Assistant Examiner* — Matthew Saunders
(74) *Attorney, Agent, or Firm* — Marshall, Gerstein & Borun LLP

(57) ABSTRACT

A magneto strictive sterilizable handpiece (14) with an electric connector (44) selectively engageable with a power cable includes a non-conducting inner core (30) having an outer surface, a conducting wire deposited on the outer surface of the inner core in a helical manner to form a coil (42) with a first end functioning as a first electrical contact and a second end functioning as second electrical contact, and an over-mold layer (50) deposited over the conducing wire to substantially completely seal the coil, so that the over-mold layer prevents a fluid from contacting any section of the conducting wire except for the first electrical contact and the second electrical contact during sterilization of the handpiece using the fluid.

15 Claims, 9 Drawing Sheets

(56) References Cited

U.S. PATENT DOCUMENTS

| | | | |
|---|---|---|---|
| 5,754,016 A * | 5/1998 | Jovanovic et al. | 318/118 |
| 6,241,520 B1 * | 6/2001 | Gofman et al. | 433/119 |
| 6,386,866 B1 | 5/2002 | Hecht et al. | |
| 6,569,109 B2 * | 5/2003 | Sakurai et al. | 601/2 |
| 6,666,860 B1 * | 12/2003 | Takahashi | 606/34 |
| 6,976,843 B2 | 12/2005 | Feine | |
| 2002/0107538 A1 * | 8/2002 | Shibata et al. | 606/169 |
| 2003/0222535 A1 * | 12/2003 | Gofman et al. | 310/316.01 |
| 2006/0188841 A1 * | 8/2006 | Edel et al. | 433/119 |
| 2008/0015551 A1 * | 1/2008 | Feine | 606/1 |

* cited by examiner

HANDPIECE FOR A MAGNETOSTRICTIVE POWER GENERATOR

FIELD OF THE INVENTION

The present invention relates generally to medical equipment and, in particular, to a design and a method of manufacturing of an ultrasonic handpiece for dental applications.

BACKGROUND TECHNOLOGY

Magnetostrictive or piezoelectric ultrasonic dental handpieces are used in dentistry to remove calculus from teeth and perform other cleaning or abrasive operations by vibrating a metal insert at an ultrasonic frequency. A dental handpiece typically receives electric current having a controlled frequency from a generator and translates the received electrical energy into a mechanical motion of the insert or a scaling tip. To this end, a magnetostrictive dental handpiece includes an electrical connector, a wire wound around a non-conducting shaft, and a housing functioning as a handle.

Ultrasonic dental handpieces may be autoclavable or non-autoclavable. Operators such as dentists or dental hygienists typically sterilize autoclavable handpieces by using steam or vaporized chemical solutions, frequently applied at a high pressure. For this reason, manufacturers typically make autoclavable handpieces detachable from their cord assemblies and/or the power generator unit. On the other hand, non-autoclavable handpieces do not tolerate high temperatures and are typically integrated with the cord assembly as well as with the power generator unit. Operators typically place disposable plastic covers over non-autoclavable handpieces to reduce contamination of the handpiece through contact with an operator's hand or with the detachable insert.

The ever-rising hygiene standards make autoclavable handpieces more preferable. Moreover, autoclavable handpieces are generally more convenient to use because they do not require temporary plastic covers. It is common knowledge that thin plastic material has a slippery feel and may interfere with the sense of a firm grip of a handle of an object, as well as reduce the overall comfort of holding the object.

Not surprisingly, autoclavable handpieces are more complex and more expensive that non-autoclavable handpieces. The manufacturing and maintenance of such handpieces also present several challenges related to protecting electrical components from heat and water damage. Today, there are several known approaches to manufacturing autoclavable handpieces. In accordance with one approach, an autoclavable handpiece includes a removable outer sheath or sleeve. An operator may sterilize the outer sheath without placing the entire handpiece into an autoclave. In an alternative approach, a handpiece includes crevices inside the housing in order to allow steam to pass through the handpiece. Unfortunately, none of these approaches allow both the convenience of sterilizing an entire handpiece without disassembly and a reliable degree of protection of the electrical components.

Further, users of electro-mechanical and magnetostrictive handpieces also find that because of the typical placement of electrical components, these handpieces are back-heavy and, as a result, cause discomfort after prolonged use. Moreover, because operators typically hold handpieces at a location closer to the scaling or cleaning tip (i.e., at the patient-proximate end), the weight of the back portion (or the patient-distal end) of the handpiece creates a significant torque making the operator's work even more tiring.

With respect to dental inserts, users of ultrasonic dental handpieces generally find it convenient to use various detachable inserts with a single handpiece. Understandably, users also prefer inter-manufacturer and inter-product compatibility and, as a result, expect inserts from different manufacturers to properly fit into the same handpiece. However, an insert designed to operate at a certain frequency may not operate properly if driven at a different frequency by the handpiece or, more precisely, by a power generator supplying electric current to the handpiece. To this end, it has been proposed to manufacture ultrasonic dental handpieces capable of adjusting the operational frequency to the particular type of insert. For example, a dental piece could drive the insert at one of the industry-standard frequencies of 25 KHz or 30 KHz, depending on the insert coupled to the handpiece. Unfortunately, this solution presents several significant challenges in production. Alternatively, some have suggested supplying dental handpieces with manual switches. A manual switch, however, similarly requires additional circuitry and increases the overall complexity of operating the handpiece. The user also needs to remember to check the type of insert and properly operate the switch to the appropriate setting or position.

SUMMARY

An autoclavable ultrasonic dental handpiece includes an inner core, a coil wound around the core, and an autoclave-resistant over-mold layer sealing the coil so that the coil is substantially completely protected from gases and liquids during sterilization.

In one aspect, the inner core has a tubular form and is made from a non-conducting material. In one embodiment, the inner core is manufactured from an engineered thermoplastic through an injection molding process. In at least some of the embodiments, a plurality of electrical connecters is insert-molded into the inner core during the injection molding process.

In another aspect, a wire made of a conducting material is wound around the inner core. The two ends of the wire connect to the two of the plurality of electrical connecters embedded in the inner core. In one embodiment, the wire is a single strand copper wire.

In another aspect, the over-molding material is pliable, tolerant of high temperatures, and otherwise suitable for autoclaving. In one embodiment, the over-molding material is a thermoplastic elastomer, such as Kraiburg TPE. In another aspect, the over-molding material has a coefficient of thermal expansion higher or equal to a coefficient of thermal expansion of the wire. In yet another aspect, the material selected for over-molding has a relatively low modulus of elasticity.

In one embodiment, the over-molding material has a sufficiently low melting point to prevent damage to the coil and, in particular, to the insulating material, during molding at a relatively high temperature. In another embodiment, the over-mold layer is formed using a single thermoset component through a potting process. In accordance with this embodiment, a liquid thermoset component is poured into a shell or a pot holding the inner core with the surrounding coil. Preferably, the selected thermoset component hardens into a solid at a room temperature. In yet another embodiment, the over-mold layer is manufactured from at least two chemical components at a room temperature. In this embodiment, one of the components may be an epoxy and the other component may be a catalyzing agent. In another embodiment, one or more thermoset components may be used in an injection molding machine.

In one embodiment, the over-molding is ergonomically shaped to provide an operator with a comfortable grip. In another embodiment, the weight of the over-mold is distributed along the longitudinal dimension of the handpiece in a manner that compensates for the weight of the electronic components at the proximal end of the handpiece.

In some embodiments, the handpiece includes a fluid conduit extending along the longitude of the handpiece. Additionally or alternatively, the handpiece includes a second conduit extending along the longitude of the handpiece to supply air to the tip of the insert. In either case, the one or more fluid conduits may couple to a single cord providing electricity, liquid, and air to the handpiece, or to several separate cords. In some embodiments, each of the cord and the handpiece may additionally include a fiberoptic conduit to supply light for curing, illumination, or for a camera mounted on the insert for up-close visual inspection. Accordingly, the handpiece may include a single, integrated cord to carry water, power, air, and light.

In some embodiments, the handpiece additionally includes an outer shell, or a sleeve. In some of these embodiments, the outer shell has a coefficient of thermal expansion higher or equal to the coefficient of thermal expansion of the over-mold layer. In other embodiments, the outer shell is made of a relatively soft material which has a lower coefficient of thermal expansion that the inner core and/or the coil. The softer outer shell absorbs the induced stresses caused by a higher thermal expansion of the inner core and/or coil when the handpiece is exposed to high temperatures.

In another aspect, the handpiece includes an insert sensing assembly to sense the type of insert coupled to the handpiece and prevent a supply of electric current to the coil if the insert is of a non-compatible type. In some embodiments, the handpiece directly prevents the coil from energizing based on the result of sensing the insert. In other embodiments, the insert sensing assembly provides a signal indicative of a type of insert sensed to a corresponding power generator which, in turn, determines whether the handpiece should operate. In one such embodiment, the handpiece includes a secondary "sensing" coil in which the current is induced during operation of the handpiece. The sensing coil in the handpiece is operatively connected to a comparator in the power generator which detects a shift in operational frequency if the frequency supplied by the power generator does not correspond to the sensed operational frequency of the insert coupled to the handpiece. The power generator shuts off the supply of current to the handpiece in response to detecting a shift in operational frequency.

If desired, the cost of manufacturing is further reduced by initially providing a single mold of the handpiece which includes one or more jumper inputs to select the operational frequency. The manufacturer may then insert a jumper to connect or disconnect an additional capacitor, for example, to adjust the operational frequency of the handpiece prior to shipping. One example of a circuit suitable for adjusting the operational frequency by means of one or more passive elements is disclosed in U.S. Pat. No. 6,976,843 to Feine, the entire disclosure of which is incorporated herein by reference. In some embodiments, the insert sensing assembly completes a secondary circuit only if the operational frequency of the insert matches the operational frequency of the handpiece. The completion of the secondary circuit in turn triggers the completion of the circuit supplying energy to the coil. Alternatively, the insert sensing assembly in another embodiment completes a secondary circuit if the operational frequency of the insert does not match the operational frequency of the handpiece, so that the completion of the secondary circuit prevents the handpiece from operating. In at least some of the embodiments, the generator supplies an audio signal if the sensing assembly of the handpiece determines that the operational frequency of the insert does not match the operational frequency of the handpiece. In other embodiments, the handpiece may be manufactured without jumper inputs.

In some embodiments, the insert sensing assembly includes a secondary coil. The secondary coil is disposed inside a hollow section or cavity of the handpiece adapted to receive a transducer stack of an insert. Accordingly, the transducer stack may be disposed at the patient-distal end of the insert. In accordance with this embodiment, the operational frequency of an insert is associated with the length of the transducer stack. The secondary coil of the handpiece is disposed near the location within the handpiece at which the tip of the transducer stack fits within the hollow section of the handpiece. In this manner, the insert sensing assembly of a handpiece configured to operate with a relatively long transducer stack enables the operation of the handpiece only if the transducer stack is long enough for at least part of the stack to be aligned with the secondary coil. Conversely, a handpiece manufactured or configured to operate with a relatively short transducer stack operates only if the transducer stack is short enough for any part of the stack not to be aligned with the secondary coil.

In some embodiments, a ferromagnetic material in the transducer stack impacts the strength of a magnetic field in the handpiece thereby changing the electric field. The secondary coil may, in turn, sense the change in the electric field. In another embodiment, the insert has an electrical component such as a wire at the patient-distal end so that the secondary coil senses electric current in the wire.

In some embodiments, the insert sensing assembly includes a pressure switch so that a sufficiently long transducer stack of a handpiece exerts pressure on the switch and enables the operation of the handpiece. In other embodiments, the insert sensing assembly includes an optical sensor. In yet other embodiments, the insert sensing assembly includes a Hall Effect switch so that a transducer stack of a handpiece exerts a magnetic field on the switch and selectively enables the operation of the handpiece. Additionally or alternatively, the insert sensing assembly may include one or more capacitor electrodes so that an associated circuit may detect a change in capacitance due to the presence of a sufficiently long insert, thereby determining whether the insert is a proper match for the handpiece.

DETAILED DESCRIPTION OF THE PREFERRED EMBODIMENTS

Figure 1:
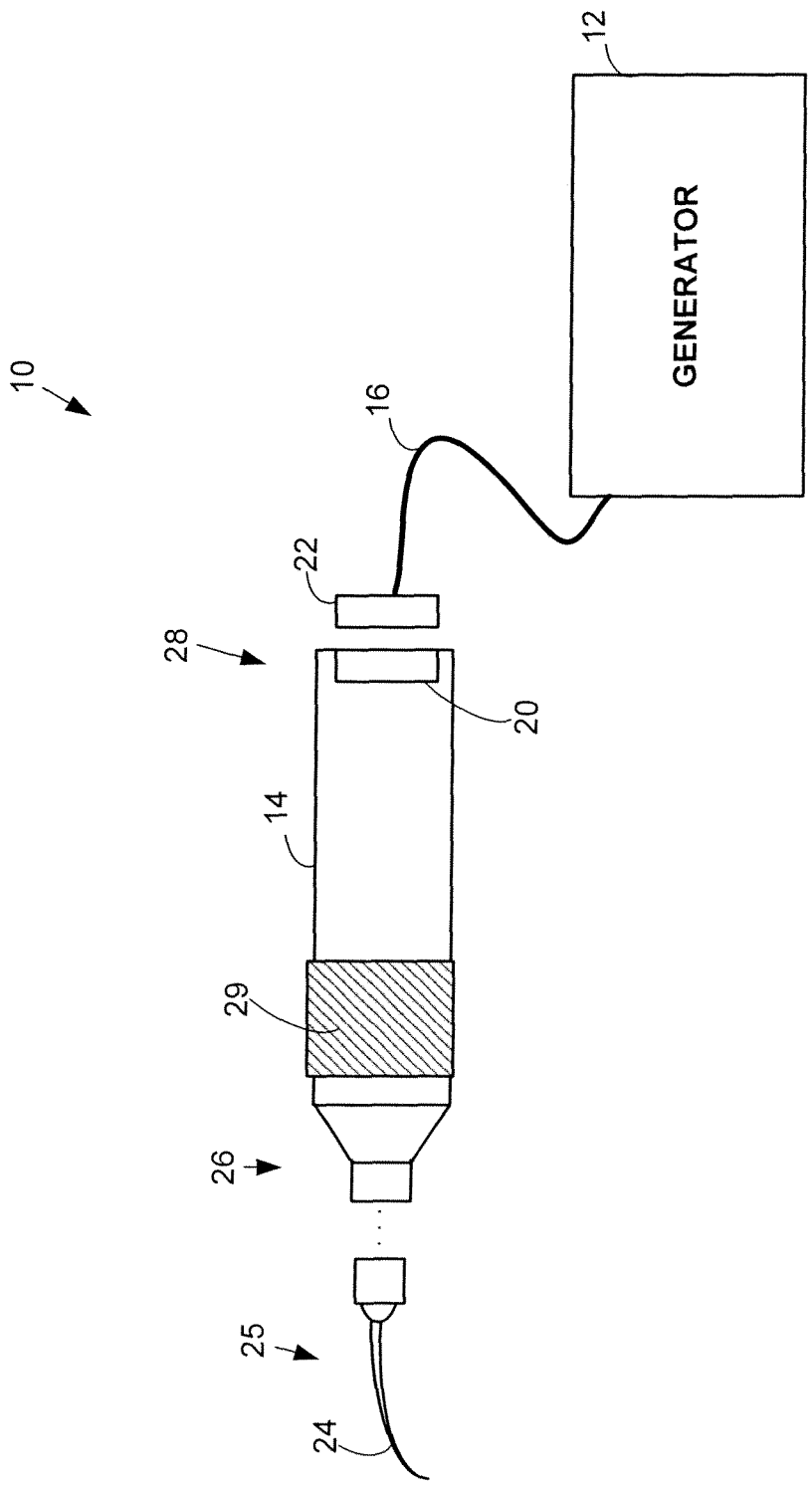
FIG. 1 schematically illustrates an ultrasonic dental system, including a signal generator and a dental insert, in which a handpiece consistent with the present disclosure may operate.

FIG. 1 illustrates an exemplary ultrasonic dental system 10. A practitioner such as a dentist may use the dental system 10 to remove calculi from a patient's teeth or to perform scaling, abrasion, and similar procedures. In particular, a generator 12 may generate pulse width modulated (PWM) or alternating electric current (AC) at a controlled, typically ultrasonic frequency such as 25 or 30 KHz. The generator 12 may then supply the current to an autoclavable handpiece 14 via a cord 16. To facilitate sterilization in an autoclave or in a similar pressurized or heated environment, the handpiece 14 may be detachable from the cord 16 or the generator 12. To this end, the handpiece 14 may be provided with a port 20 including one or more electrical connectors and, optionally, a fluid connector to receive a supply of liquid, air, or both. A fiberoptic conduit may additionally allow the handpiece 14 to receive inserts adapted to supply light to the mouth cavity and, possibly, to carry the reflected light out of the mouth cavity for conducting an up-close inspection during dental operations. In this manner, the dental system 10 may work in co-operation with a camera which may process the images from the mouth cavity. Accordingly, the power cord 16 may include a connector 22 which may mate with the port 20. Alternatively, the handpiece 14 may engage multiple cords, such as an electric cord and a fluid supply cord.

In some embodiments, the handpiece 14 and the cord 16 may form an integral autoclavable unit. In particular, the cord 16 may be permanently attached to the handpiece 14 so that the resulting handpiece/cord assembly does not require the port 20 or the connector 22. Instead, the handpiece 14 and the cord 16 may not expose any wire ends or other metal components in a section where the cord 16 is coupled to the handpiece 14. It will be further appreciated that manufacturing the handpiece 14 and the cord 16 as an integral unit may simplify the design of these components and accordingly reduce the cost of manufacturing the handpiece/cord assembly. Moreover, integrating the cord 16 with the handpiece 14 may simplify the process of autoclaving by eliminating the need to detach the handpiece 14 from the cord 16 each time an operator decides to sterilize the handpiece 14. In accordance with these embodiments, the cord 16 may include a durable insulating material capable of tolerating high temperatures and/or pressure experienced in an autoclave procedure.

The handpiece 14 may translate the electrical energy received from the generator 12 into mechanical energy by generating an electro-magnetic field and applying this field to a vibrating or otherwise movable component. In particular, the handpiece 14 may vibrate a tip 24 of an insert 25 at a frequency dependent on the driving AC frequency supplied by the generator 12, the physical dimensions of the tip 24, and the internal circuitry of the handpiece 14. Although illustrated in FIG. 1 as an integral component, the insert 25 may include several parts, some of which may be further detachable. One of ordinary skill in the art will also appreciate that the transducer for converting the energy supplied by the generator 12 into a vibratory motion of the tip 24 may be disposed in the handpiece 14, in the insert 25, or in a separate component interacting with the handpiece 14 and the insert 25.

The handpiece 14 may have a tubular, rectangular, or other elongated form. The insert 25 may engage the handpiece 14 at a patient-proximal end 26. Accordingly, the port 20 may be disposed at the patient-distal end 28. The operator may hold the handpiece 14 at or about the grip section 29. Although the grip section 29 may be integral with the body of the handpiece 14, FIG. 1 schematically illustrates a removable grip made of a different material than the external layer of the handpiece 14. As discussed in greater detail below, at least the middle section of the handpiece 14 may be ergonomically shaped to provide an easy grip for the operator. Additionally, the weight of the handpiece 14 may be distributed in a substantially even manner from the patient-proximal end 26 to the patient-distal end 28.

Figure 2:
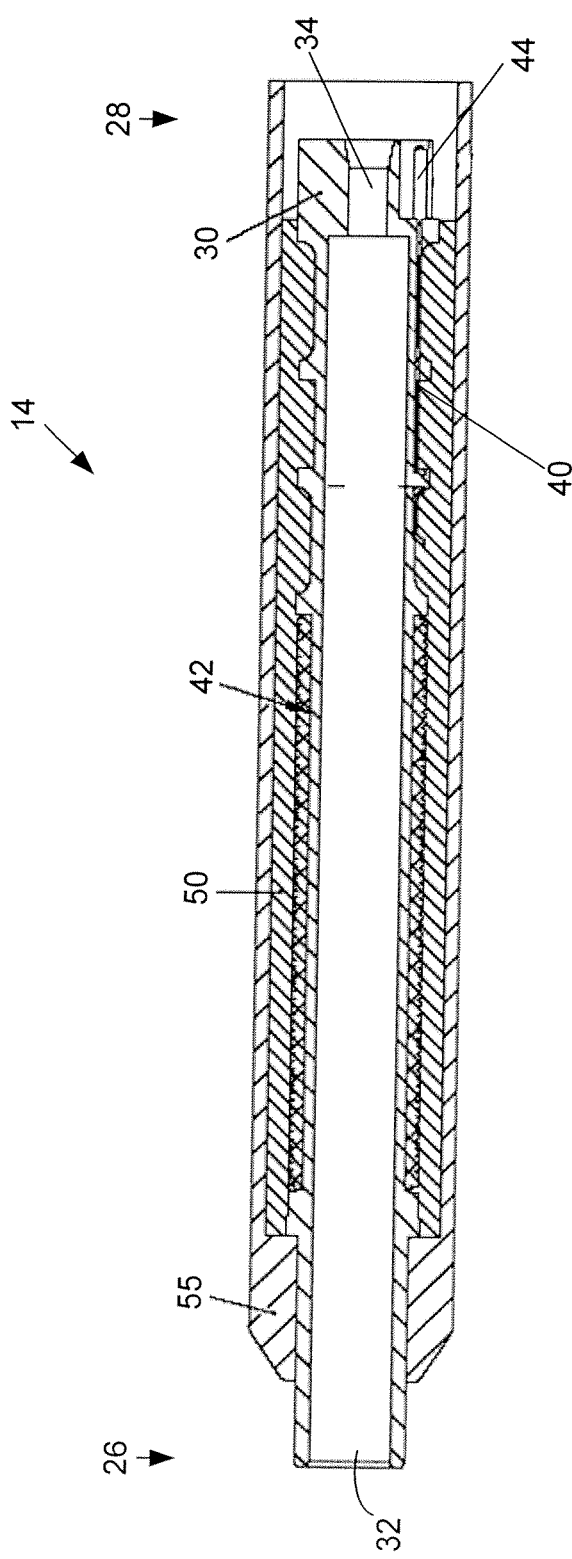
FIG. 2 is a schematic sectional view of the ultrasonic magnetostrictive handpiece illustrated in FIG. 1.

Referring to a sectional view of the handpiece 14 illustrated in FIG. 2, a shaft or an electrically non-conducting core 30 may have a cylindrical shape, with the radius of the (preferably) right cylinder disposed perpendicularly to the horizontal axis of the handpiece 14 (additionally or alternatively, the core 30 may be thermally non-conducting). In one possible embodiment, the core 30 may be manufactured using injection molding process. More specifically, a molten material may be injected into a mold at a high pressure. A suitable material for manufacturing the core 30 may be an engineered thermoplastic such as Ultem™ resin-grade CR5-5011, for example. However, it will be appreciated that the core 30 may be manufactured using any suitable method, including the methods currently known in the art.

In some embodiments, the core 30 may be solid. However, in the embodiment illustrated in FIG. 2, the core 30 includes a channel 32 to allow fluid passage from the patient-distal end 28 to the patient-proximal end 26. Because some of the energy supplied by the generator 12 may be converted into heat, both the patient and the clinician may experience discomfort or pain due to the heating of the tip 24 and the handpiece 14. To remove the generated heat from the insert 25, the channel 32 may supply liquid such as water to the operating surface on the tooth via the insert 25. As illustrated in FIG. 2, the channel 32 may receive fluids through a fluid connector 34 at the patient-distal end 28 of the handpiece 14. It will be further appreciated that in other possible embodiments, the core 30 may have a substantially solid body with several narrow channels extending along the horizontal axis of the handpiece 14. For example, the core 30 may be adapted to supply both water and air to the tooth surface via an air channel and a liquid channel, respectively.

A wire 40 may be wound around the core 30 in a spiral or helical manner to form a coil 42. The wire 40 may be, for example, a single strand copper wire. Each pair of ends of each strand of the wire 40 may be soldered or otherwise permanently connected to the port 20. To enable the flow of current generated by the generator 12 through the coil 42, the port 20 may include a set of electrical connectors 44. In addition to providing connections to the terminals of the connector 22, the set of electrical connectors 44 may include jumper inputs for configuring such additional operational parameters as the frequency of mechanical vibration of the tip 24. To this end, the set of electrical connectors 44 may include additional connectors or pins. For example, the port 20 may include pins 1-4. The first and the second ends of the wire 40 may connect to pins 1 and 4, respectively. A jumper (not shown) may optionally connect to pins 3 and 4 of the connector set 44. In one embodiment, the jumper may be a capacitor having a value selected to reduce the operational frequency of the handpiece by a controlled amount. Thus, if the jumper is not connected to the connector set 44, the handpiece 14 may operate at a first operational frequency such as 30 KHz. On the other hand, if the jumper is connected to the connector set 44, the handpiece 14 may operate at a second, reduced operational frequency such as 25 KHz.

In other embodiments, the connector set 44 may include only two connectors and the switching of operational frequency may be supported by other means. Alternatively, the handpiece 14 may be manufactured to operate with only one frequency. Further, it will be appreciated that the connector 22 may be an integral part of the core 30. Thus, in at least some of the possible embodiments, the connector 22 is merely a logical designation of a section of the core 30 which engages the cord 16. Meanwhile, in other embodiments, the connector 22 may be manufactured separately and may be installed into the core 30 at one of the stages in assembling the handpiece 14. It will be further appreciated that the connector 22 may provide additional protection to the coil 42. In particular, the connector 22 may expose leads made of a heat- and moisture-tolerant metal to the external surface of the handpiece 14 which may be different from the metal in the wire 40. To this end, the ends of the wire 40 may be soldered to the inside of the connector 22 in a manner preventing the water, a cleaning solution used in an autoclave, or other chemicals from reaching the wire 40 from the outside.

In accordance with one possible embodiment, the port 20 may be insert-molded into the core 30. In this case, the ends of the wire 40 may contact the connector set 44 inside the core 30. To this end, the core 30 may be molded with one or more openings or bores through which the ends of the wire 40 may be inserted to contact the internal components of the port 20. Alternatively, the ends of the wire 40 may be inserted into the core 30 only after molding the core 30 and insert-molding or otherwise inserting or attaching the port 20. This embodiment of the handpiece 14 may thereby offer additional protection to the wire 40 from exposure to chemical vapors or liquids.

Next, an over-mold layer 50 may be deposited over the coil 42. In the embodiments discussed below, the over-mold layer 50 may substantially completely surround the coil 42 while leaving only wire ends in the connector set 44 exposed as the corresponding pins. Thus, the over-mold layer 50 may protect the coil 42 from water or other chemicals to which the handpiece 14 is exposed during sterilization or during operation. Additionally, the over-mold layer 50 may hold the coil 42 firmly in place, thereby reducing the damage to the internal components of the handpiece 14 incurred through mechanical shock in operation of the dental system 10. In other words, the over-mold layer 50 may increase the overall rigidity of the structure of the handpiece 14.

In one embodiment, the over-mold layer 50 is made from a thermo-plastic elastomer (TPE). For example, the over-mold layer 50 may be composed of Kraiburg TPE. As one of the possible alternatives, the over-mold layer 50 may be formed using a thermoset material such as silicone. As one of ordinary skill in the art will appreciate, several types of silicone are commercially available. It is also generally known that silicone is relatively expensive. However, silicone may withstand temperatures in the autoclaving range, making it a suitable material for sealing the coil 42 in a manner that will withstand numerous sterilization cycles. Moreover, silicone has an additional advantage of being strong and durable. In general, a thermoset material such as silicone is a relatively pliable material. The particular type of silicone to be used in the over-mold layer 50 may be selected in view of such additional factors as durometer, for example. In some embodiments, the silicone of approximately durometer 40 to 60 may be selected. As one familiar with the durometer scale will recognize, a material with a hardness of durometer 40 is about as responsive to indentation as as a pencil eraser and a material with durometer 60 may be compared to the threads of an automobile tire. Of course, other types of silicone with lower or higher durometer values may be similarly used.

In another possible embodiment, the over-mold layer 50 is formed by potting, or embedding, the core 30 and the coil 42 using one or more encapsulation or potting compounds. In general, the process of potting a device involves placing the device in a tray or mold and pouring a liquid compound into the tray. Preferably but not necessarily, the potting is conducted at room temperature to reduce the risk of damage to the coil 42 and other electro-mechanical components of the handpiece 14. In at least one contemplated embodiment, two or more chemicals are poured into a mold in which the core 30 and the coil 42 are placed. In accordance with this embodiment, the two or more chemicals undergo a chemical reaction to form a compound which cures (hardens) at room temperature. An example of such compound may be a two-part urethane such as Hysol® M-06FL or a two-part epoxy such as Hysol® M-31CL, both available from the Henkel corporation of Düsseldorf, Germany and Rocky Hill, Conn.

Other types of materials, such as thermoset compounds, can be similarly used to form the over-mold layer 50. As one of ordinary skill in the art will recognize, thermosets generally cure at a faster rate through exposure to heat. Generally, thermosets cure through a chemical reaction with another agent. In some cases, a thermoset may be mixed with a corresponding agent prior to depositing the mixture in a mold. In these cases, the mixture is typically kept at a relatively low temperature to prevent a premature chemical reaction between the thermoset and the agent. In most cases, thermosets, once cured, may be better suited for high-temperature applications because they do not melt like thermoplastics. If one or more thermoset materials are used to form the over-mold layer 50 by means of heating and pouring the liquefied thermoset compounds into a mold, these materials preferably have a melting lower than the melting point of the insulation of the wire 40.

It is further contemplated that the over-mold layer 50 may be formed using extrusion, blow molding, and other manufacturing techniques. However, irrespective of the particular method of manufacturing or depositing the over-mold layer 50, at least the external surface of the coil 42 is substantially completely covered by the over-mold layer 50. In particular, the over-mold layer 50 should effectively prevent fluids and dust particles from interacting with the coil 42. Also, the over-mold layer 50 in most of the contemplated embodiments should withstand a substantial number of steam autoclaving cycles. In consideration of the cost of manufacturing the handpiece 14 and of the general inconvenience of replacing defective handpieces, the over-mold layer 50 preferably withstands at least 1000 steam cycles.

Referring to FIG. 2, an outer shell 55 may surround the over-mold layer 50 in an up-featured embodiment of the handpiece 14. The outer shell 55 may be manufactured from a hard plastic. For example, the outer shell 55 may be an engineered thermoplastic material. In one possible embodiment, the outer shell 55 is firmly affixed to the over-mold layer 50 by means of an adhesive. In another embodiment, the over-mold layer 50 is machined to include grooves on the external surface. The outer shell 55 may include corresponding threads on the inner surface so that the over-mold layer 50 can be easily screwed onto the over-mold layer 50. In yet another alternative, the outer shell 55 may be held in place by friction with the over-mold layer 50. In either case, the outer shell 55 may provide a tight fitting over the over-mold layer 50 to eliminate crevices and other forms of interstices between these two layers. It is contemplated that the fitting may be tight enough to prevent substantially all moisture and gas from entering the inside of the handpiece 14, but since achieving such a moisture-tight and gas-tight fitting is difficult, the over-molding of the coil advantageously avoid corrosive damage or shorts that may otherwise be caused by moisture or gas contacting the coil. As yet another alternative, the outer shell 55 may be deposited over the over-mold layer 50 to form a single layer. For example, the outer shell 50 may be an element or compound chemically reacting with the material of the over-mold layer 50 to form another type of plastic, rubber, or other material. To this end, the material corresponding to the outer shell 50 may be liquefied and poured over the over-mold layer 50, or deposited over the outer shell 50 using potting, dipping, or other available techniques.

Although the outer shell 55 may provide additional protection to the internal components of the handpiece 14 as well as a firmer feel for the benefit of the operator, the outer shell 55 may not be provided at all in at least some of the contemplated embodiments. In this case, the over-mold layer 50 may effectively become the external layer exposed to the operator. As indicated above, the material may be selected for the over-mold layer 50 in view of such factors as cost, heat tolerance, hardness, etc. In those embodiments where the operator makes direct contact with the over-mold layer 50, the material for this layer is preferably also pleasing to touch.

Alternatively, the outer shell 55 may be used instead of the over-mold layer 50. In other words, the shape of the outer shell 55 and the thermal qualities of the material used to manufacture the outer shell 55 may be such that the inner core 30 and the coil 42 are sufficiently protected from water and other chemicals without the use of the over-mold layer 50. In this case, the outer shell 55 may be deposited onto the inner core 30 and the coil 42 by means of potting or molding, similar to the methods discussed above in reference to the over-mold layer 50.

In the embodiments excluding the outer shell 55, the over-mold layer 50 may be ergonomically shaped in at least those sections where the operator holds the handpiece 14. For example, the over-mold layer 50 may have a curvature and one or more indentations suitable for the operator's fingers. Preferably, the shape of the over-mold layer 50 is also aesthetically pleasing. To this end, the over-mold layer 50 may contain one or coloring elements. Alternatively, the over-mold layer 50 may be painted after the completing the step potting, sealing, or molding.

As discussed above in reference to FIGS. 1 and 2, the patient-distal end 28 may include one or several relatively heavy electro-mechanical components such an ultrasonic transducer, for example. Additionally, the port 20 may include metal components making the patient-distal end 28 heavier than the patient-proximal end 26 and thus less convenient for the operator. In other embodiments, the distribution of weight of the internal components such as the core 30, the port 20, and the coil 42 may be substantially uniform along the horizontal axis of the handpiece 14. However, because the operator typically holds the handpiece 14 at a section closer to the patient-proximal end 26, the momentum or the torque produced by the patient-distal end 28 of the handpiece 14 may create an undesirable sensation of holding a back-heavy instrument. Moreover, the weight of the connector 22 coupled to the port 20, as well as some of the weight of the cable 16, may increase the torque even further during operation of the dental system 10. To address these problems, the over-mold layer 50 may be molded or potted over the inner core 30 and the coil 42 in a non-uniform manner. In particular, a larger amount of a material included in the over-mold layer 50 may be placed at the patient-proximal end 26. In this embodiment, a greater thickness of the over-mold layer 50 at or near the patient-proximal end 26 may effectively compensate for the weight distribution of other components of the handpiece 14. Alternatively, the over-mold layer 50 may have a constant thickness but a varying density along the horizontal axis of the handpiece 14 to distribute more weight of the over-mold layer 50 to the patient-proximal end 26. In another embodiment, the over-mold layer 50 may be potted or molded in such away as to make the proximal end 26 heavier than other sections of the handpiece 14. In this sense, the over-mold layer 50 may over-compensate for the weight of the other components and thus create a forward-heavy weight distribution within the handpiece 14. The center of gravity of the handpiece 14 may be thus spaced closer to the patient-proximal end 26 than to the patient-distal end 28 by a certain percentage of the length of the handpiece 14 as measured along its horizontal axis. For example, the handpiece 14 may be manufactured to have a center of gravity at about 15% to 20% closer to the patient-proximal end 26 to the patient-distal end 28 than a comparable non-sterilizable handpiece.

In some embodiments, the outer shell 55 may not form a continuous layer over the over-mold layer 50. For example, one section of the outer shell 55 may be disposed near the patient-proximal end 26 and another section of the outer shell 55 may be disposed near the patient-distal end 28, with the over-mold layer 50 exposed in the area between the two section of the outer shell 55. This configuration may be preferable if for example, the cost of the outer shell 55 is relatively high but the protection afforded by the outer shell 55 in the fragile parts of the handpiece 14 is nevertheless desirable. One of ordinary skill in the art will further appreciate that other configurations of the outer shell 55 in view of cost, ergonomics, and cosmetic considerations are also possible.

Figure 3:
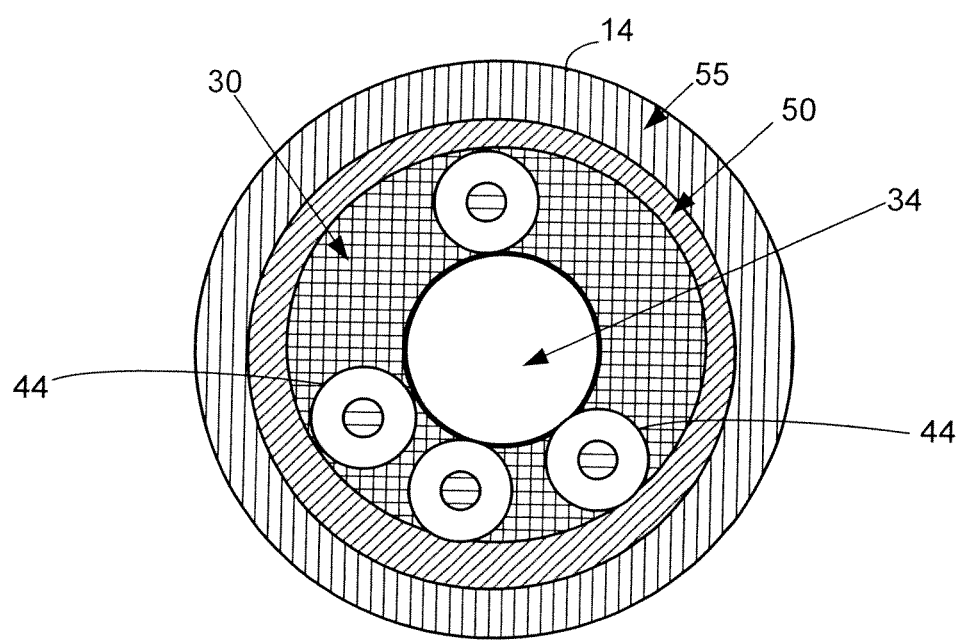
FIG. 3 is a rear view of the ultrasonic magnetostrictive handpiece illustrated in FIG. 2.

FIG. 3 illustrates a rear view of the handpiece 14 corresponding to the embodiment illustrated in FIG. 2. As seen from the patient-distal, or rear, perspective, the handpiece 14 includes four electrical connectors 44 placed around the fluid connector 34. The electrical connectors 44 may be similarly disposed in a row or in any other geometrical arrangement. Similarly, the fluid connector 34 may not be centered with respect to the rear circular surface of the handpiece 14; however, it is contemplated that providing the fluid connector 34 and the channel 32 at or near the center of the cylindrical body of the handpiece 14 may improve the weight-distribution and the overall ergonomic characteristic of the handpiece 14.

Figure 4:
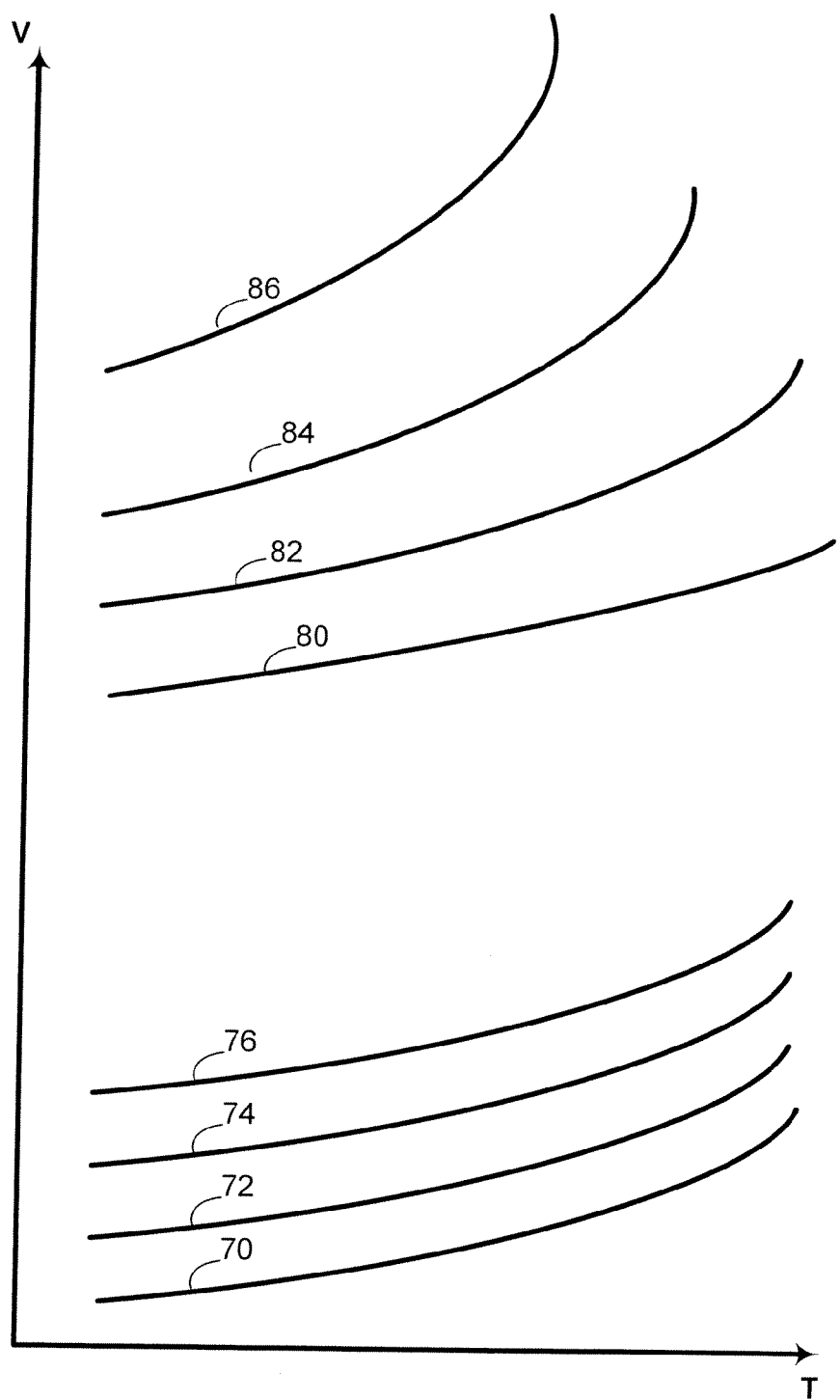
FIG. 4 illustrates several exemplary relationships between coefficients of thermal expansion of several components or layers of the ultrasonic magnetostrictive handpiece illustrated in FIGS. 1-3.

To further reduce the probability of causing damage to the handpiece 14 during sterilization, the materials for the core 30, the coil 42, and the over-mold 50 may be selected in view of the respective coefficients of thermal expansion. Because the handpiece 14 undergoes sterilization at a high temperature, each of the materials used in the manufacturing of the handpiece 14 may expand. This expansion may damage the handpiece 14 if the materials used in manufacturing the handpiece 14 expand at significantly different rates. FIG. 4 illustrates some of the relationships between coefficients of thermal expansions of the materials forming the core 30, the coil 42, the over-mold 50, and the outer shell 55. In particular, the graphs 70-76 illustrate a preferred relationship between the thermal expansion qualities of the core 30, the coil 42, the over-mold 50, and the outer shell 55. In accordance with this selection of materials, each of these materials expands at about the same rate, thus preserving the spatial relations between the components. For example, the graph 70 illustrates the expansion of the core 30, the graph 74 illustrates the expansion of the coil 42, and the graph 74 illustrates the expansion of the over-mold layer 50. In those embodiments where the outer shell 55 is additionally provided, the expansion of the material forming the outer shell corresponds to the graph 76. It will be noted, however, that a selection of materials having the properties illustrated in graphs 70-76 are relatively difficult to achieve in practice.

In another embodiment, the materials selected for the components 30, 42, 50, and 55 may not expand at an approximately the same rate corresponding to the graphs 72-76. For example, a graph 80 may correspond to the thermal expansion of the core 30 and a graph 82 may correspond to the thermal expansion of the coil 42. As indicated by the graphs 80 and 82, the coil 42 may undergo a larger expansion at a certain temperature than the core 30. However, because the coil 42 is disposed along the external surface of the 30, this expansion may be relatively safe for the structure of the handpiece 14. Analogously, graphs 84 and 86 illustrate an exemplary thermal expansion of the over-mold 50 and of the outer shell 55, respectively. For the reasons outlined above with respect to the graphs 80 and 82, the selection of materials corresponding to the graphs 80-86 may be acceptable for the manufacturing and maintenance of the handpiece 14 because of the relative placement of the layers. On the other hand, if the core 30 includes a material expanding either by a greater percentage at a given temperature or at a greater rate than the coil 42, the handpiece 14 may not be able to undergo sterilization in an autoclave, or may degrade after fewer sterilization cycles than other embodiments.

In yet another embodiment, the material forming the coil 42 may expand at a higher rate than the material selected for the over-mold 50. Accordingly, the coil 42 may exert a force on the over-mold 50 during sterilization in a high-temperature environment. To prevent or, at least, reduce damage to the handpiece 14, the material of the over-mold 50 may be relatively soft and pliable. Thus, the over-mold 50 may effectively absorb the stress of thermal expansion of the coil 32. In accordance with this embodiment, the core 30 may similarly have a higher coefficient of thermal expansion than the over-mold 50.

It will be appreciated that the graphs 70-76 and 80-86 provide only a schematic and approximate illustration of the preferred thermal qualities of the materials involved in manufacturing the handpiece 14. As a result, these graphs do not reflect some of the additional factors which a manufacturer may consider. In particular, each of the graphs 70-76 and 80-86 corresponds to a volume of a material as a function of temperature. Additionally, the manufacturer may consider the rate of change of volume with this respect of temperature, or the first derivative of the each of the graphs 70-76 and 80-86. Similarly, one of ordinary skill in the art will appreciate that several other factors may be considered and that the examples discussed in reference to FIG. 4 are not meant to be exhaustive.

Figure 5B:
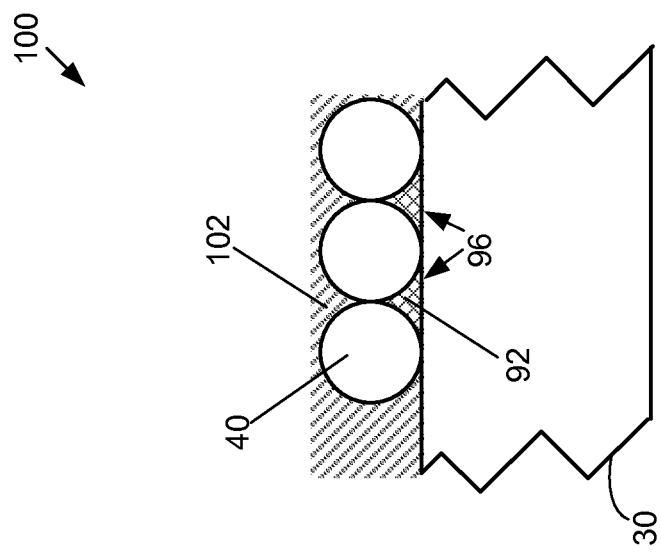
FIGS. 5A and 5B illustrate exemplary arrangements of an over-mold layer of the ultrasonic magnetostrictive handpiece illustrated in FIGS. 1-3.
Figure 5A:
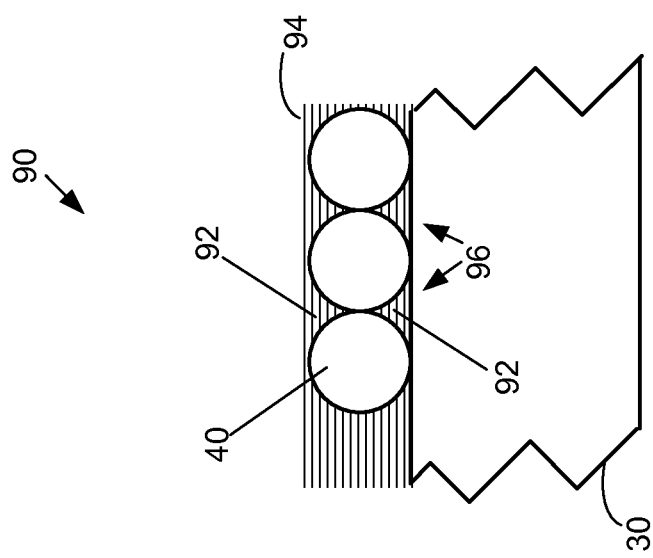

As noted above, the over-mold layer 50 may be manufactured using one of several possible methodologies. To further clarify, FIG. 5A illustrates an exploded view of a wire 40 wound around a section of the inner core 30 in accordance with several contemplated embodiments. In particular, a section 90 may be formed by pouring one or more compounds into a mold or a tray in which the core 30 and the wire 40 are placed. Thus, as illustrated in FIG. 5A, a material 92 may form both an outer protective sub-layer 94 covering the wire 40 and fill the interstices 96 between loops of the wire 40 and the external surface of the core 30. On the other hand, as illustrated in FIG. 5B, a section 100 may be formed by depositing a layer of sealing material 102 over the wire 30. In this embodiment, the sealing material 102 may be shaped into an appropriate form prior to being deposited over the wire 30. One of ordinary skill in the art will recognize that in this embodiment, the sealing material 102 may be shaped by means of extrusion, molding, or any other suitable methodology. Meanwhile, the interstices 96 may be filled with the same material or with a compound 92, for example. In the latter case, the sealing material 102 preferably covers the coil 42 at both terminal loops to prevent moisture from entering the interstices 96.

Figure 6:
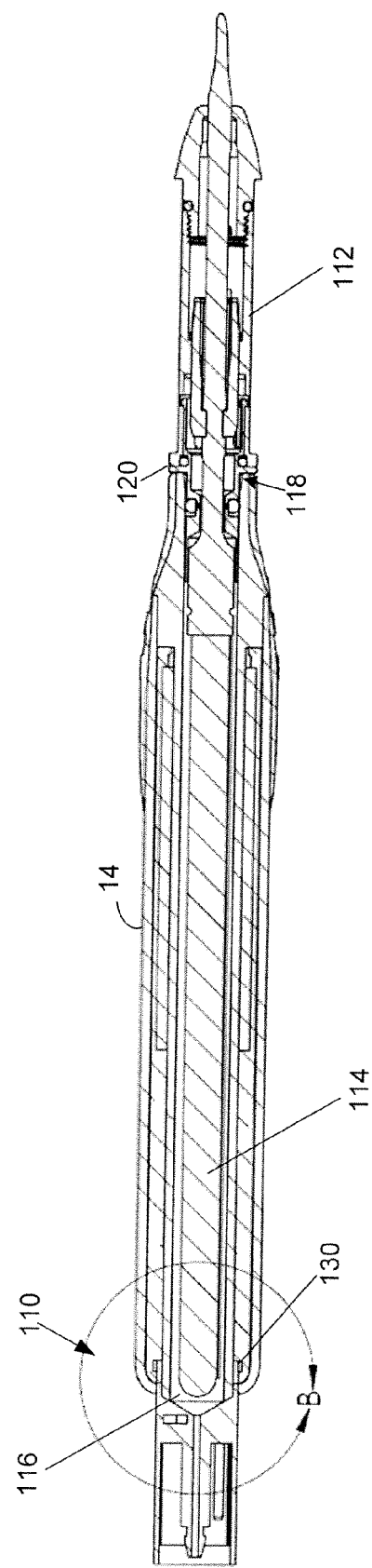
FIG. 6 schematically illustrates an electrically compatible insert coupled to a handpiece consistent with the present disclosure.

Referring to FIG. 6, the handpiece 14 may also include a sensing assembly 110 for sensing the type of insert being used and selectively enabling the operation of the handpiece 14. In particular, an insert 112 may have a transducer stack 114 having a substantially cylindrical shape with a diameter selected so as to tightly pass through the opening 118 and fit inside a hollow section or cavity 116 of the handpiece 14. In the example configuration illustrated in FIG. 6, the insert 112 may be a 25 KHz insert and, as a result, the transducer stack 114 may be relatively long. A lip 120 may limit the extent to which the transducer stack 114 can penetrate the cavity 116. With the insert 112 installed, at least a portion of the stack 114 is aligned with a secondary (sensing) coil 130.

In operation, the transducer stack 114 may induce electric current in the secondary coil 130. The resulting electric signal may, in turn, activate an electric switch (not shown) such as a transistor to enable the flow of current from the generator 12 to the coil 42. In one contemplated embodiment, the switch may be a part of the connector assembly 20. However, the switch is preferably a part of the circuitry of the generator 12, as discussed in greater detail below. In this case, the cord 16 may include an additional wire carrying a signal from the secondary coil 130.

Figure 7:
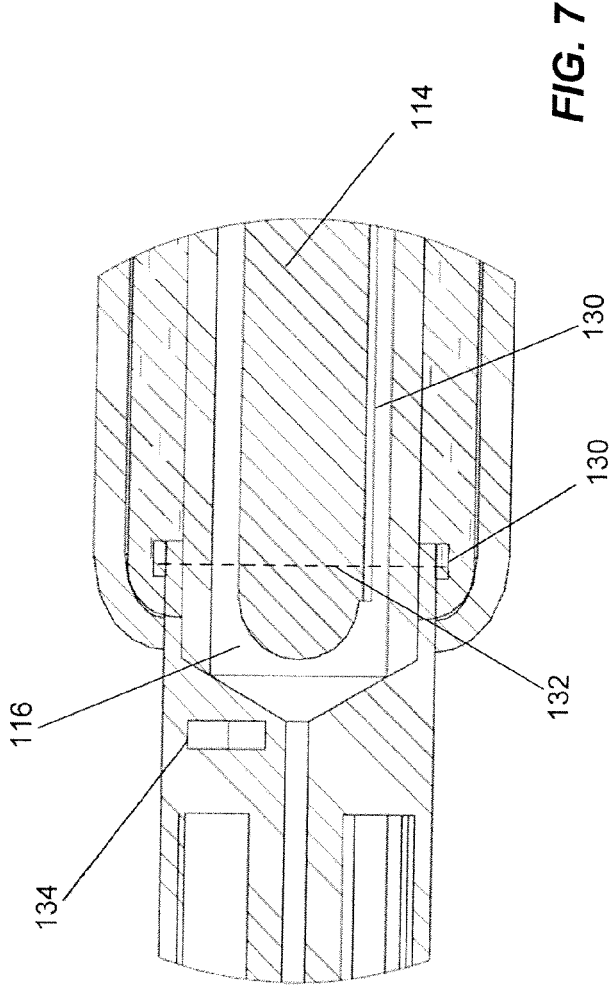
FIG. 7 is an exploded view of an insert sensing system of a handpiece in cooperative arrangement with the insert illustrated in FIG. 6.

A portion of the handpiece 14 including the sensing assembly 110 is shown in an enlarged view in FIG. 7. In particular, FIG. 7 illustrates more clearly that the length of the insert 114 allows the coil 130 to sense at least the tip of the insert 114. In one possible embodiment, the coil 130 may establish a magnetic field approximately along the cross-section 132, so that the presence of ferromagnetic material of the transducer stack 114 will create a variation in the magnetic field and have a noticeable effect on the current in the secondary coil 130. Alternatively, a Hall Effect sensor 134 may similarly detect a variation in the magnetic field as a result of proximity to the transducer stack 114. As another alternative, the transducer stack 114 may selectively make physical contact with a pressure switch (not shown). In this embodiment, the pressure switch may be disposed at the patient-distal end of the cavity 116. A relatively long transducer stack would apply physical pressure upon the pressure switch once the corresponding insert is installed in the handpiece 14. Similar to the secondary coil 130, Hall Effect sensor 134, or any other type of sensor used with the handpiece 14, the pressure switch may operate an electrical or mechanical switch to enable the flow of current through the coil 42.

In another embodiment, the insert sensing assembly 110 may include an optical sensing assembly (not shown) disposed approximately along a diameter of the circular cross section 132. A radiation source such as an LED, for example, may be at one end of the diameter and emit a small amount of radiation. A radiation or an optical sensor such as a photodiode may sense the signal emitted by the radiation source to complete a circuit of the insert sensing assembly 110. Thus, a relatively long transducer stack may prevent the radiation sensor from detecting a signal from the radiation source while a relatively short transducer stack may allow the optical sensing assembly to complete the circuit.

Figure 8:
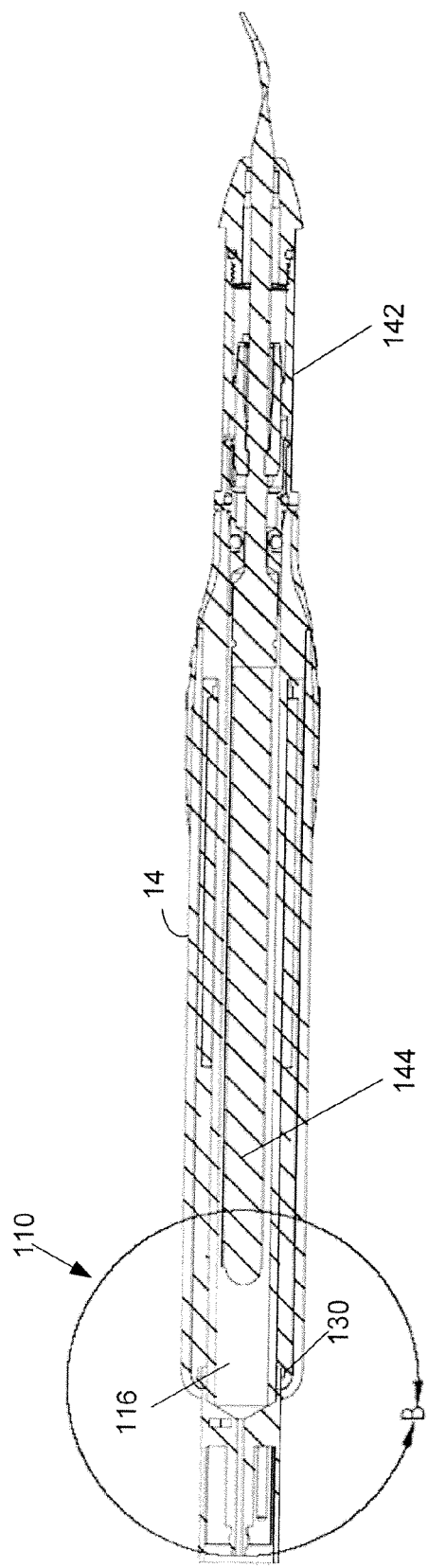
FIG. 8 schematically illustrates an electrically incompatible insert coupled to a handpiece consistent with the present disclosure.
Figure 9:
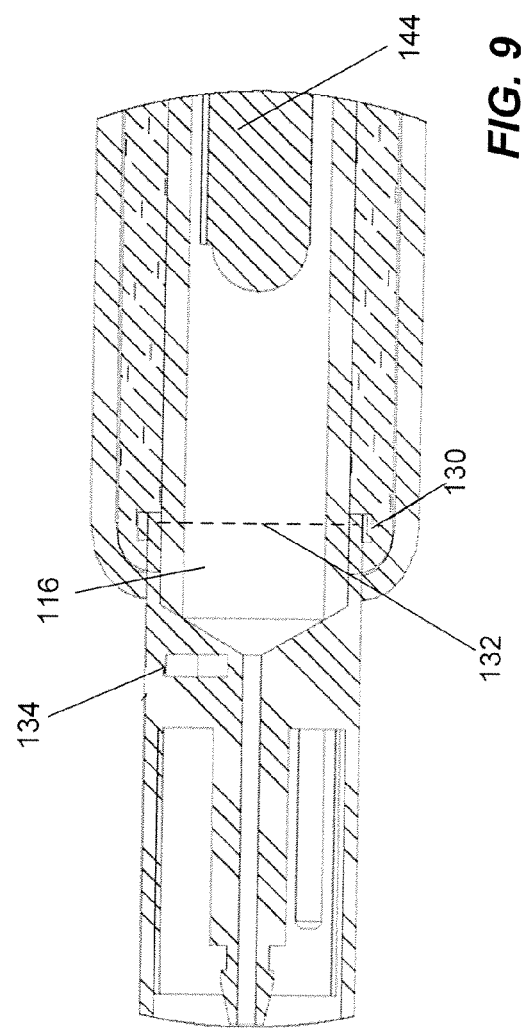
FIG. 9 is an exploded view of an insert sensing system of a handpiece in cooperative arrangement with the insert illustrated in FIG. 6.

FIG. 8 illustrates the handpiece 14 with an insert 142 which may operate at 30 KHz and, accordingly, include a relatively short transducer stack 144. It is common for 30 KHz transducers to be shorter by approximately 0.5 inches than 25 KHz transducers. However, it will be appreciated that the difference in length may be significantly greater or smaller in some possible implementations. Moreover, it will be noted that the operational frequencies of 25 KHz or 30 KHz are discussed herein by way of example only, and that the handpiece 14 as well as the generator 12 may similarly operate with other frequencies suitable for dental operations. To better illustrate the interaction of the insert 142 with the handpiece 14, FIG. 9 provides a more detailed view of the sensing assembly 110 and the transducer stack 144. In contrast to the configuration illustrated in FIG. 6, no part of the transducer stack 144 aligns with the coil 130. Thus, the sensing assembly 110 may generate a signal indicative of an absence of a long transducer stack. The additional circuitry of the handpiece 14 or of the generator 12 may accordingly enable or disable the flow of current through the coil 42.

To take one specific example, an operator may intend to use the handpiece 14 as a 25 KHz scaler. To configure the handpiece 14, the manufacturer may connect pins 3 and 4 of the electrical connector set 44 with a jumper wire to select the operational frequency of the handpiece 14. As discussed above, this configuration will effectively require the use of a 25 KHz insert with the handpiece 14. If, at some point, the user inadvertently inserts a 30 KHz insert into the handpiece 14, the mistake may not be immediately apparent to the user: because the diameter of the transducer stack of the 30 KHz insert may be the same as a diameter of a 25 KHz insert the transducer of the wrong insert may properly pass through the opening 118 and, moreover, the entire length of the transducer stack of the 30 KHz insert may properly fit inside the cavity 116. However, the sensor assembly 110 will detect the mismatch and prevent the coil 42 from energizing. This will alert the user to the fact, or at least the possibility, that he or she has installed a wrong insert into the handpiece 14. Equally importantly, the patient will not experience the discomfort caused by a mismatch in the corresponding operational frequencies of the handpiece and of the insert.

Referring generally to FIGS. 6-9, an output signal generated by the insert sensing assembly 110 may operate an electric switch to selectively enable or disable vibration of an insert 112 or 142 when the user turns on the handpiece 14 by operating an "on" button or a footswitch, for example (neither switch shown). As indicated above, a manufacturer will configure the circuitry the handpiece 14 to operate only at a specific frequency such as 25 KHz, for example. In this case, the insert sensing assembly 110 may be configured to unconditionally disable or unconditionally enable the operation of the handpiece 14, depending on whether a long transducer stack has been detected. For example, the manufacturer may set the operational frequency of a handpiece to 30 KHz. The handpiece 14 may operate if the insert sensing assembly 110 does not detect a long transducer stack. Therefore, in this particular configuration, a signal indicative of absence of a long transducer stack, coupled with a configuration or a signal indicative of a 30 KHz selection, may enable the flow of current through the coil 42. However, the manufacturer may alternatively configure a similar handpiece 14 (or the same mold of the handpiece 14) to operate at 25 KHz. In this configuration, a signal indicative of presence of a long transducer stack may enable the flow of current through the coil 42.

Figure 10:
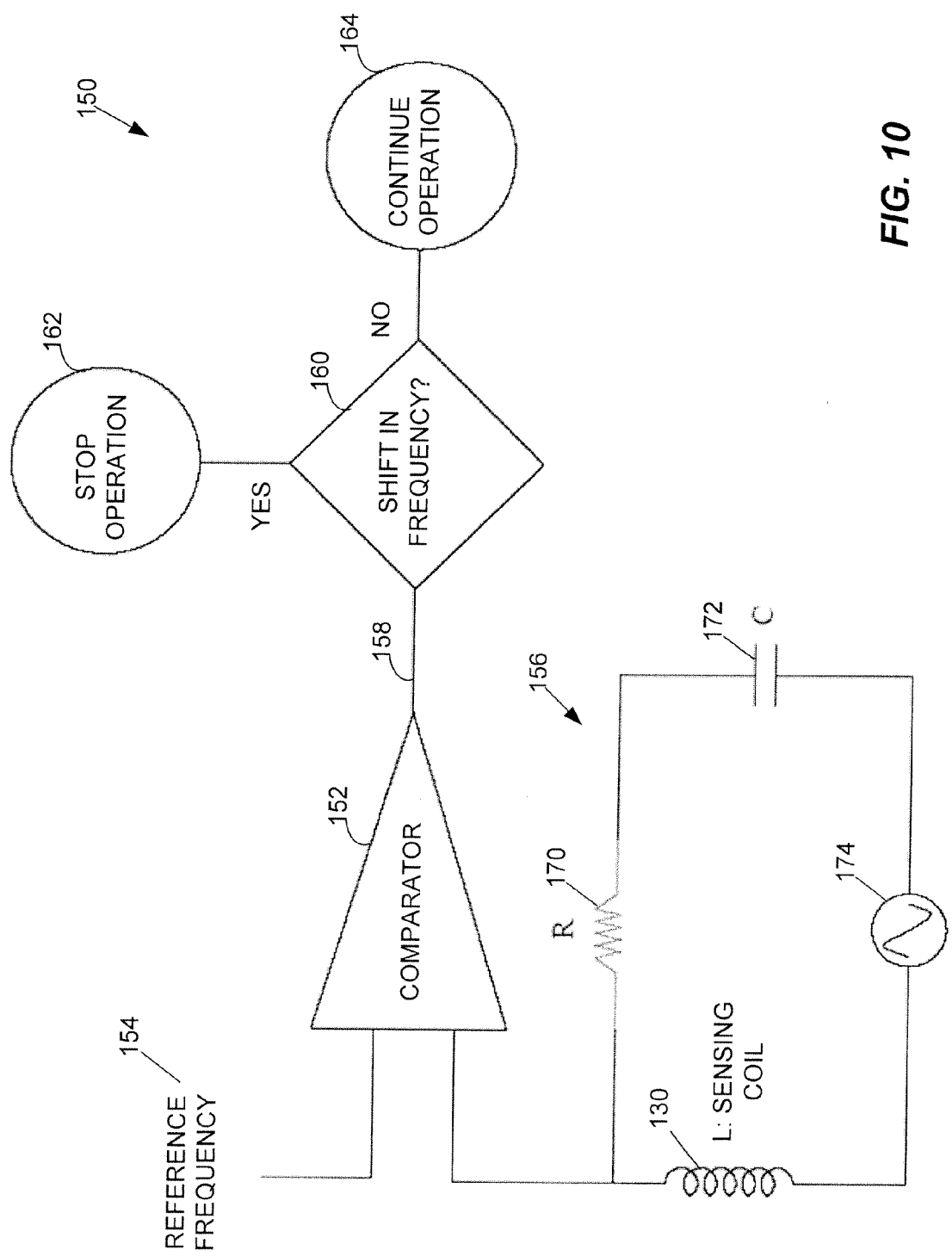
FIG. 10 is a schematic of an example circuit for sensing the frequency associated with an insert coupled to a handpiece of FIG. 1-3 or 6-9, comparing the sensed frequency to a reference frequency, and selectively disabling the operation of the handpiece based on the result of comparing the frequencies.

FIG. 10 illustrates an example combined control circuit and logic diagram 150 for selectively enabling or disabling the operation of the handpiece 14. In operation, a comparator 152 may compare the reference frequency 154 to an output of a sensing circuit 156 to generate a signal 158. To continue with one of the examples discussed above in reference to FIGS. 6-9, the reference frequency 154 may be 25 KHz. In particular, the generator 14 may produce an electric current of the reference frequency 154 to drive the coil 42. The user may accordingly purchase a handpiece 14 configured to operate at 25 KHz. Thus, if the operator uses a proper insert with the 25 KHz handpiece 14, the frequency of the current induced in the sensing circuit 156 will be the same as the reference frequency 154, and the comparator 154 will detect a substantial alignment in frequency and output a corresponding signal 158.

In a block 160, the combined control circuit and logic diagram 150 may check whether the signal 158 indicates a shift in frequency or an alignment in frequency. If the frequencies do not match, the handpiece will not operate (block 162). Conversely, the handpiece 14 will continue to operate if no shift in frequency is detected (block 164).

Figure 11:
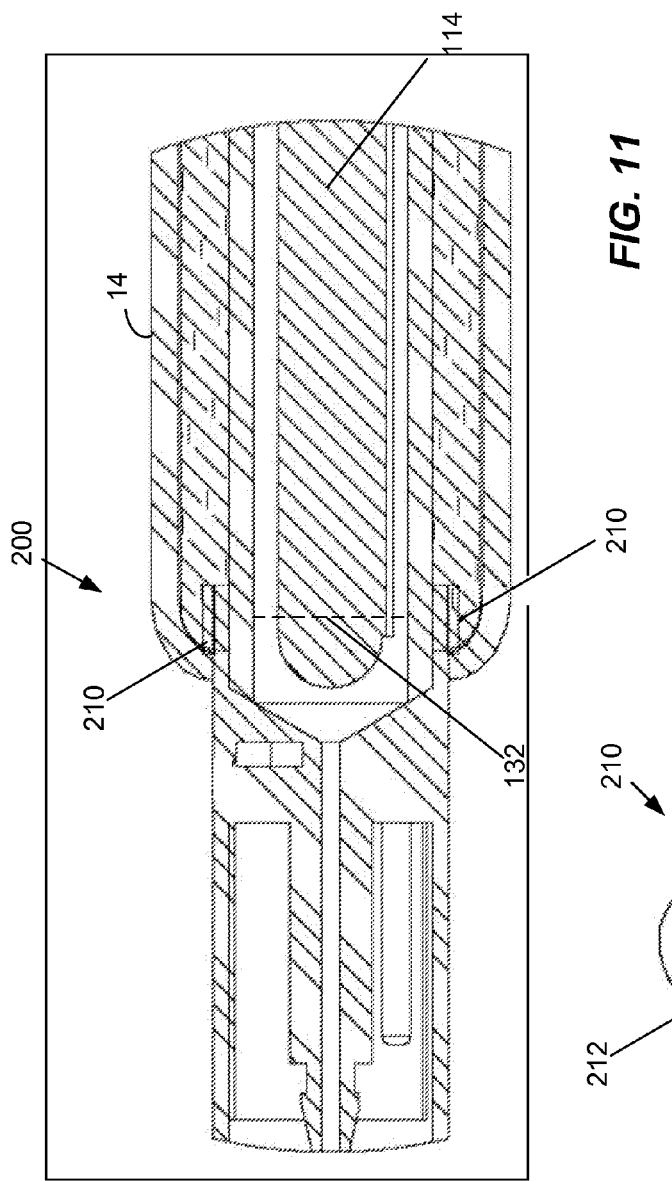
FIG. 11 is an exploded view of another embodiment of an insert sensing system of a handpiece in cooperative arrangement with an insert.
Figure 12:
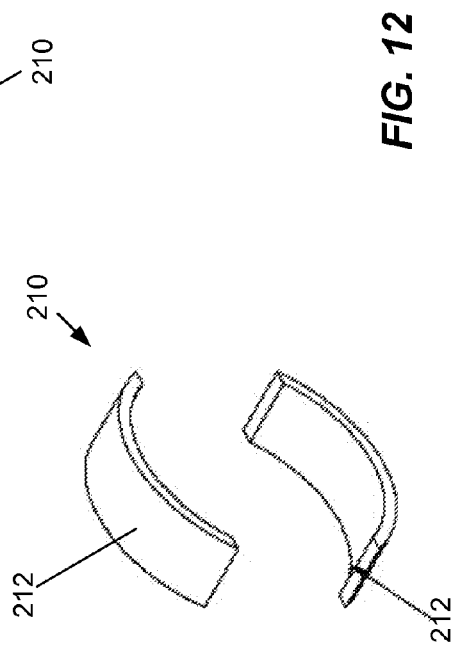
FIG. 12 illustrates a pair of capacitor electrodes that may be used in the insert sensing system illustrated in FIG. 11.

The control circuit 150 may include one or more components of the insert sensing assembly 110: for example, FIG. 10 illustrates the sensing coil 130 (see FIGS. 8 and 9) as one of the components of the sensing circuit 156. Additionally, the sensing circuit 156 may include one or more resistors 170, one or more capacitors 172, and an alternate current source with a set frequency 174. It should be noted that a design engineer may set the frequency of the current source 174 to any desired value. In operation, the current source 174 may then set the frequency of the sensing coil 130 but, due to the changes in inductance of the sensing coil 130, the actual frequency of a signal that the sensing circuit 156 supplies to the comparator 152 will deviate from the frequency set by the current source 174. It will be appreciated that the circuit 156 may be any type of a suitable RLC (i.e., resistor-inductor-capacitor) circuit. Further, it will be noted that the sensing circuit 156 may detect the presence or absence of a transducer stack of a certain length by using other electrical components. FIGS. 11 and 12 illustrate one such approach utilizing capacitor electrodes.

Referring to FIG. 11, a sensing assembly 200 be similar to the embodiments of the sensing assembly 110 discussed above in reference to FIGS. 6-9. However, the sensing assembly 200 may include a capacitance sensor 210 to sense a presence or absence of a relatively long transducer stack 114. In particular, the electrodes 210 would have one capacitance value if the tip of the transducer stack 114 reaches the cross-section 132 and a different capacitance value if a shorter transducer stack does not reach the cross-section 132. A corresponding RLC circuit, designed according to the principles known in the art, may generate a signal indicative of the amount of charge, of the amount of time required to accumulate a certain charge, or both.

FIG. 12 illustrates the capacitance sensor 210 in greater detail. In this example embodiment, the capacitance sensor 210 may include a pair of electrode capacitors 212. Each of the electrode capacitors 212 may be a metal (e.g., copper) plate bent into a concave shape to envelop a section of the circumference of the circular core 30. Alternatively, the radius of curvature of the electrode capacitors 212 may be smaller so that the electrode capacitors 210 may fit inside the core 30, or greater so that the electrode capacitors 212 may envelop one or more of the layers of the handpiece 14 in addition to the core 30. In operation, the dielectric properties of an area between the plates of the electrode capacitors 212 may vary in accordance with a presence or an absence of a transducer stack along the cross-section 132, thereby controlling the amount of charge accumulated on the electrode capacitors 212.

Thus, the handpiece 14 may use one or more of the many types of sensors, including those known in the art. Further, it will be appreciated that a corresponding circuit, such as the sensing circuit 156, for example, may be distributed among the components of the system 10 in a number of ways. Referring back to FIG. 10, each of the components 170, 172, and 174 may reside inside the generator 12, with only the sensing coil 130 disposed in the handpiece 14. Alternatively, one or more of the components 170-174 may be disposed inside the handpiece 14, with the rest of the components 170-174 remaining in the generator 12. Still further, some or all of the logic corresponding to the comparator 152 and to the blocks 160-164 may be implemented in the handpiece 14; however, the generator 12 preferably implements the control logic to reduce the complexity, weight, and cost of the handpiece 14.

Referring still to FIG. 10, some of the embodiments discussed above may not require at least some of the components of the sensing circuit 156 or of the combined control circuit and logic diagram 150. For example, if the sensing assembly 110 includes a pressure sensor or an optical sensor, the sensing circuit 156 may not require inductive or capacitive components. Instead, the sensing circuit 156 may simply include an electric switch such as a transistor, and the optical switch or the pressure switch may operate the electric switch to selectively open or close a circuit supplying current to the coil 42. Other implementations using the techniques known in the art are also possible.

In some embodiments, the generator 12 or the handpiece 14 may provide an audio signal to the user indicating that a signal from the insert sensing assembly 110 or 200 has disabled the operation of the handpiece 14. Additionally, or alternatively, the generator 12 or the handpiece 14 may include a visual indicator such as an LED which may illuminate or blink if a wrong insert has been detected. In some embodiments, the circuitry for providing an audio and/or visual indication of a wrong insert type may be included in the handpiece 14 and the generator 12 may simply generate electric current to drive the coil 42. In other embodiments, this circuitry may be provided in the generator 12 to reduce the complexity, cost, and weight of the handpiece 14.

It will be further appreciated that the sensing assembly 110 may be similarly used in a non-autoclavable handpiece. Moreover, the sensing assembly 110 may operate with inserts having operational frequencies other than 25 or 30 KHz discussed above with respect to the example embodiments.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this disclosure, which would still fall within the scope of the claims.

What is claimed is:

1. An ultrasonic dental handpiece operatively engageable with a detachable insert of a first or of a second type, the handpiece comprising:
   a housing having a cavity for receiving a detachable insert;
   an insert sensing assembly for generating a first insert signal in response to detecting a detachable insert with a transducer stack having a first length corresponding to a first operational frequency and a second insert signal in response to detecting a detachable insert with a transducer stack having a second length corresponding to a second operational frequency, respectively; and
   a drive circuitry for vibrating the detachable insert, wherein the drive circuitry is configured to operate only at a fixed operational frequency of the handpiece matching the first operational frequency, and wherein the drive circuitry operates if the insert sensing assembly generates the first signal, and does not operate if the insert sensing assembly generates the second signal.

2. The handpiece of claim 1, wherein the dental handpiece is a magnetostrictive handpiece further comprising:
   an electrical connector for receiving an electric signal having a drive frequency from a generator; and
   wherein the drive circuitry includes a first conducting coil for generating an electro-magnetic field based on the electric signal, the first insert signal is indicative of the first length of the transducer stack and the second insert signal is indicative of the second length of the transducer stack.

3. The handpiece of claim 2 in combination with a detachable insert that has a transducer stack having the first length, wherein the first length is greater than the second length.

4. The handpiece of claim 2, wherein the housing has a patient-proximate end and a patient-distal end; wherein the housing engages a detachable insert at the patient-proximate end; wherein the insert sensing assembly includes a secondary coil disposed at a particular distance from the patient-proximate end; and wherein a current is induced in the secondary coil only if a length of the transducer stack of a detachable insert is equal or greater than the particular distance.

5. The handpiece of claim 1, wherein the insert sensing assembly includes a pressure switch operable upon by a transducer stack of a detachable insert.

6. The handpiece of claim 1, wherein the insert sensing assembly includes a pair of capacitor electrodes to detect presence of a transducer stack having a greater length of one of a first length and a second length.

7. The handpiece of claim 1, wherein the handpiece produces one of an audio signal or a visual signal if the drive circuitry does not operate when a detachable insert of a transducer having a second length is present in the cavity.

8. A magnetostrictive handpiece for performing ultrasonic dental operations, the handpiece having a fixed drive frequency and comprising:
   a housing having a cavity for receiving a transducer stack of a detachable dental insert having an operational frequency, wherein the operational frequency depends on a length of the transducer stack;
   an insert sensing assembly to generate an insert signal when the transducer stack of the detachable dental insert is inside the cavity, based on the length of the transducer length;
   an electrical connector for receiving an electric signal; and
   a first conducting coil disposed inside the housing and adapted to generate an electro-magnetic field from the received electric signal only if the insert signal received from the insert sensing assembly is indicative of a correspondence between the fixed drive frequency and the operational frequency.

9. The handpiece of claim 8, wherein the insert signal is a binary signal.

10. The handpiece of claim 8, wherein the handpiece is sterilizable.

11. The handpiece of claim 8, wherein the received electric signal has a fixed drive frequency, the handpiece further comprising:

a drive frequency selector for changing the first drive frequency to a second drive frequency.

12. A method of operating an ultrasonic dental handpiece having a fixed operational frequency, comprising:

receiving an electric signal at the handpiece;

when a dental insert with a transducer stack is inserted into the handpiece, determining whether the dental insert is of a first type corresponding to a first length of the transducer stack and a first operational frequency matching the fixed operational frequency of the handpiece or of a second type corresponding to a second length of the transducer stack and a second operational frequency, including sensing a length of the transducer stack of the inserted dental insert; and using the received electrical signal to vibrate the dental insert at the first operational frequency only if the dental insert is of the first type.

13. The method of claim 12, wherein sensing the length of the transducer stack of the dental insert includes sensing the length through one of an inductance coil, a pressure switch, a Hall Effect sensor, a capacitance sensor, or an optical sensor.

14. The method of claim 12, wherein receiving the electric signal at the handpiece includes receiving the electric signal from a power generator; and wherein determining whether the dental insert is of the first type associated with the fixed operational frequency or of the second type associated with the second operational frequency includes supplying an insert sensing signal to the power generator.

15. The method of claim 12, wherein using the received electric signal to vibrate the dental insert at the first operational frequency includes automatically operating an electric switch based on a result of determining whether the dental insert is of the first type or of the second type.

* * * * *

UNITED STATES PATENT AND TRADEMARK OFFICE
CERTIFICATE OF CORRECTION

PATENT NO.       : 8,678,820 B2
APPLICATION NO. : 12/922399
DATED            : March 25, 2014
INVENTOR(S)      : Jamnia et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 676 days.

Signed and Sealed this

Twenty-ninth Day of September, 2015

Michelle K. Lee
*Director of the United States Patent and Trademark Office*